(12) United States Patent
Pines et al.

(10) Patent No.: US 7,235,401 B2
(45) Date of Patent: Jun. 26, 2007

(54) METHOD FOR DETERMINING CELL CYCLE POSITION

(75) Inventors: Jonathon Noe Pines, Cambridge (GB); Nicholas Thomas, South Glamorgan (GB); Anne Elizabeth Jones, South Glamorgan (GB); Ian David Goodyer, South Glamorgan (GB); Michael John Francis, South Glamorgan (GB); Rahman Aziz Ismail, South Glamorgan (GB); Jonathan Mark Kendall, South Glamorgan (GB)

(73) Assignees: GE Healthcare UK Limited, Amersham (GB); Cancer Research Technology Limited, London (GB)

( * ) Notice: Subject to any disclaimer, the term of this patent is extended or adjusted under 35 U.S.C. 154(b) by 0 days.

(21) Appl. No.: 10/491,762

(22) PCT Filed: Sep. 12, 2002

(86) PCT No.: PCT/GB02/04258

§ 371 (c)(1),
(2), (4) Date: Aug. 6, 2004

(87) PCT Pub. No.: WO03/031612

PCT Pub. Date: Apr. 17, 2003

(65) Prior Publication Data

US 2004/0248133 A1  Dec. 9, 2004

(30) Foreign Application Priority Data

Oct. 5, 2001  (GB) ................. 0123856.7

(51) Int. Cl.
*C12N 15/00* (2006.01)
*C12N 5/00* (2006.01)
*C12N 5/22* (2006.01)
*C12Q 1/00* (2006.01)
*C12P 21/06* (2006.01)

(52) U.S. Cl. .................. 435/320.1; 435/325; 435/366; 435/367; 435/455; 435/4; 435/69.1; 514/2; 536/23.1; 536/23.4; 530/350

(58) Field of Classification Search ...................... None
See application file for complete search history.

(56) References Cited

U.S. PATENT DOCUMENTS

| | | | | |
|---|---|---|---|---|
| 6,159,691 A * | 12/2000 | La Thangue et al. | ........... | 435/6 |
| 6,461,813 B2 * | 10/2002 | Lorens | ......................... | 435/6 |
| 6,764,852 B2 * | 7/2004 | Cornelis et al. | ............. | 435/325 |
| 2002/0137699 A1 * | 9/2002 | Mueller et al. | ............... | 514/44 |

FOREIGN PATENT DOCUMENTS

GB  WO0157237  *  9/2001

OTHER PUBLICATIONS

Piaggio et al. Structrue and growth-dependent regulation of the human cyclin B1 promoter.□□Exp Cell Res. vol. 216, No. 2, pp. 396-402, Feb. 1995.*

King et al. Mutagenic analysis of the destruction signal of mitotic cyclins and structural charaterization of ubiquitinated intermediates. Mol Biol Cell. vol. 7, No. 9, pp. 1343-1357, Sep. 1996.*

Piaggio et al, Structure and Growth-Dependent Regulation of the Human Cyclin B1 Promoter, Experimental Cell Research 216:396-402, 1995.*

Darnell et al, Molecular Cell Biology, Third Edition, 1998 Scientific American Boooks, pp. 291-303.*

Maniatis et al, Molecular Cloning: A Laboratory Manual, Second Edition, 1989 Cold Spring Harbor Laboratory Press, pp. 16.3-16.15.*

Doetschman, T., Interpretation of phenotype in genetically engineered mice. Lab. Animal Sci. 49:137-143, 1999,□□.*

Mateus, Carolina, et al. "Destabilized green fluorescent protien for monitoring dynamic changes in yeast gene expression with flow cytometry" Yeast, vol. 16, No. 14, Oct. 2000 pp. 1313-1323.

* cited by examiner

*Primary Examiner*—David Guzo
*Assistant Examiner*—Walter Schlapkohl
(74) *Attorney, Agent, or Firm*—Yonggang Ji (57) ABSTRACT

The invention provides a novel, non-destructive and dynamic process for determining the cell cycle position of living cells. The invention also provides DNA constructs, and cell lines containing such constructs, that exhibit activation and deactivation of a detectable reporter molecule in a cell cycle specific manner. The invention thus allows greater precision in determining cell cycle phase status than existing techniques and further provides a method for continuous monitoring of cell cycle progression in individual cells.

6 Claims, 9 Drawing Sheets

METHOD FOR DETERMINING CELL CYCLE POSITION

CROSS REFERENCE TO RELATED APPLICATIONS

This application is a filing under 35 U.S.C. § 371 and claims priority to international patent application number PCT/GB02/04258 filed Sep. 12, 2002, published on Apr. 17, 2003 as WO03/031612, and to foreign application number 0123856.7 filed in Great Britain on Oct. 5, 2001, the entire disclosures of which are hereby incorporated by reference.

TECHNICAL FIELD

The present invention relates to a novel, non-destructive and dynamic process for determining the cell cycle position of living cells.

BACKGROUND TO THE INVENTION

Eukaryotic cell division proceeds through a highly regulated cell cycle comprising consecutive phases termed G1, S, G2 and M. Disruption of the cell cycle or cell cycle control can result in cellular abnormalities or disease states such as cancer which arise from multiple genetic changes that transform growth-limited cells into highly invasive cells that are unresponsive to normal control of growth. Transition of normal cells into cancer cells can arise though loss of correct function in DNA replication and DNA repair mechanisms. All dividing cells are subject to a number of control mechanisms, known as cell-cycle checkpoints, which maintain genomic integrity by arresting or inducing destruction of aberrant cells. Investigation of cell cycle progression and control is consequently of significant interest in designing anticancer drugs. (Flatt, P. M. and Pietenpol, J. A. Drug Metab. Rev., (2000), 32(3–4), 283–305; Buolamwini, J. K. Current Pharmaceutical Design, (2000), 6, 379–392).

Accurate determination of cell cycle status is a key requirement for investigating cellular processes that affect the cell cycle or are dependent on cell cycle position. Such measurements are particularly vital in drug screening applications where:

i) substances which directly or indirectly modify cell cycle progression are desired, for example, for investigation as potential anti-cancer treatments;

ii) drug candidates are to be checked for unwanted effects on cell cycle progression; and/or iii) it is suspected that an agent is active or inactive towards cells in a particular phase of the cell cycle.

Traditionally, cell cycle status for cell populations has been determined by flow cytometry using fluorescent dyes which stain the DNA content of cell nuclei (Barlogie, B. et al, Cancer Res., (1983), 43(9), 3982–97). Flow cytometry yields quantitative information on the DNA content of cells and hence allows determination of the relative numbers of cells in the G1, S and G2+M phases of the cell cycle. However, this analysis is a destructive non-dynamic process and requires serial sampling of a population to determine cell cycle status with time. Furthermore, standard flow cytometry techniques examine the total cell population in the sample and yield limited data on individual cells, which precludes study of cell cycle status of different cell types that may be present within the sample under analysis.

EP 798386 describes a method for the analysis of the cell cycle of cell sub-populations present in heterogeneous cell samples. This method uses sequential incubation of the sample with fluorescently labelled monoclonal antibodies to identify specific cell types and a fluorochrome that specifically binds to nucleic acids. This permits determination of the cell cycle distribution of sub-populations of cells present in the sample. However, as this method utilises flow cytometry, it still yields only non-dynamic data and requires serial measurements to be performed on separate samples of cells to determine variations in the cell cycle status of a cell population with time following exposure to an agent under investigation for effects on cell cycle progression.

A further disadvantage of flow cytometry techniques relates to the indirect, and inferred assignment of cell cycle position of cells based on DNA content. Since the DNA content of cell nuclei varies through the cell cycle in a reasonably predictable fashion, ie. cells in G2 or M have twice the DNA content of cells in G1, and cells undergoing DNA synthesis in S phase have an intermediate amount of DNA, it is possible to monitor the relative distribution of cells between different phases of the cell cycle. However, the technique does not allow precision in determining the cell cycle position of any individual cell due to ambiguity in assigning cells to G2 or M phases and to further imprecision arising from inherent variation in DNA content from cell to cell within a population which can preclude precise discrimination between cells which are close to the boundary between adjacent phases of the cell cycle. Additionally, variations in DNA content and DNA staining between different cell types from different tissues or organisms require that the technique is optimised for each cell type, and can complicate direct comparisons of data between cell types or between experiments (Herman, Cancer (1992), 69(6), 1553–1556). Flow cytometry is therefore suitable for examining the overall cell cycle distribution of cells within a population, but cannot be used to monitor the precise cell cycle status of an individual cell over time.

Cell cycle progression is tightly regulated by defined temporal and spatial expression, localisation and destruction of a number of cell cycle regulators which exhibit highly dynamic behaviour during the cell cycle (Pines, J., Nature Cell Biology, (1999), 1, E73–E79). For example, at specific cell cycle stages some proteins translocate from the nucleus to the cytoplasm, or vice versa, and some are rapidly degraded. For details of known cell cycle control components and interactions, see Kohn, Molecular Biology of the Cell (1999), 10, 2703–2734.

Figure 1:
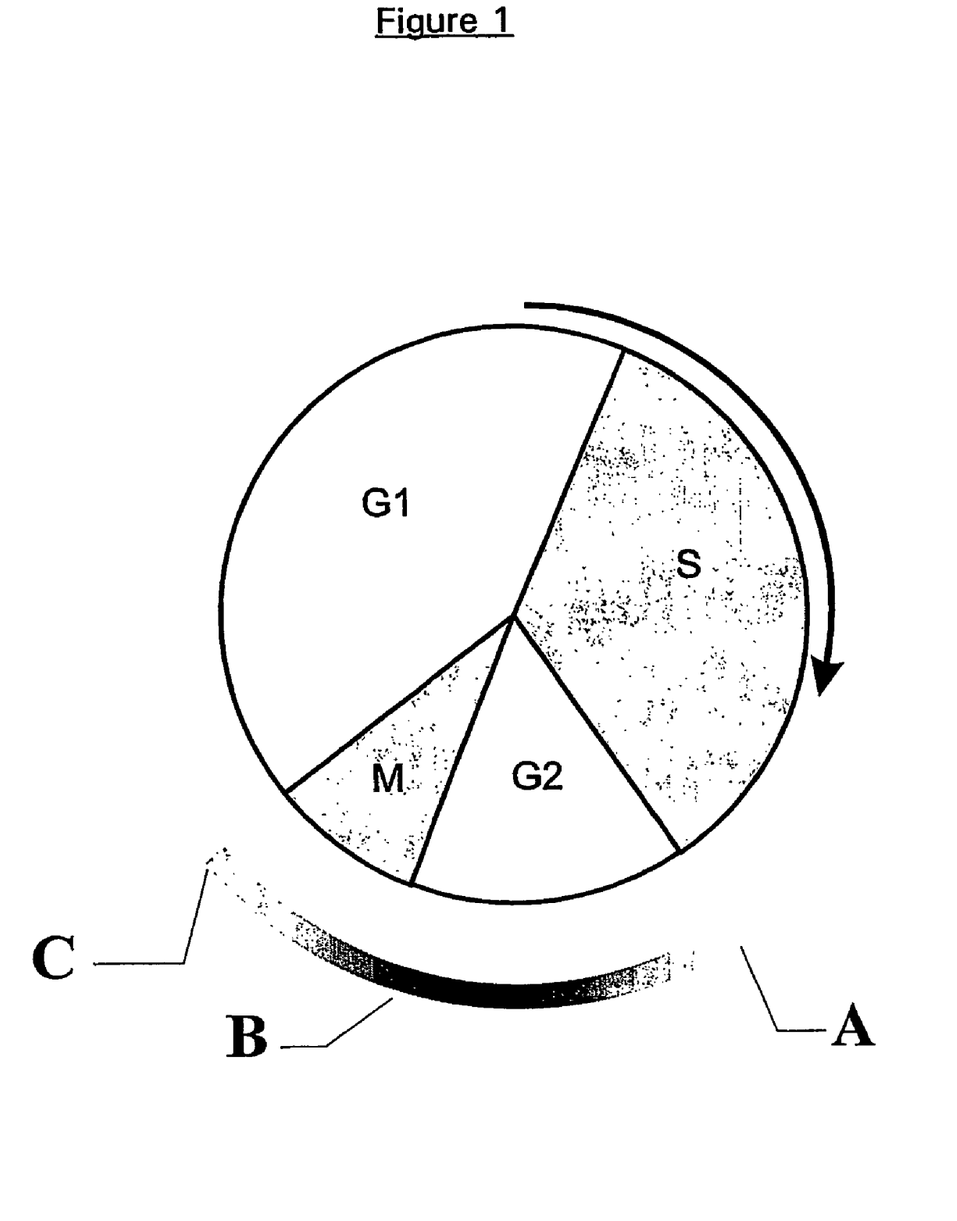
FIG. 1 is a schematic diagram illustrating cyclin B1 regulation during cell cycle progression. The cell cycle proceeds in the direction of the arrow with cyclin B1 expression driven by a cell cycle phase-specific promoter which initiates expression at the end of the S phase and peaks during G2 (A). At the start of mitosis (B) cyclin B1 translocates from the cytoplasm to the nucleus and from metaphase onwards (C) the protein is specifically degraded.

One of the most extensively characterised cell cycle regulators in human cells is cyclin B1, temporal and spatial expression and destruction of which controls cell transition from G2 to M and its exit from M. Cyclin B1 expression is driven by a cell cycle phase specific promoter which initiates expression at the end of S phase and peaks during G2. Once expressed, this protein constantly shuttles between the nucleus and the cytoplasm during the G2 phase, but it is primarily cytoplasmic because the rate of its export is much greater than its import. At the start of mitosis, cyclin B1 rapidly translocates into the nucleus, when its rate of import substantially increases, and its export decreases, in a phosphorylation dependent manner (FIG. 1). Thus, the localisation of cyclin B1 in the cell can be used to mark the transition from G2 phase to mitosis. Once a cell reaches metaphase, or, more accurately, when the spindle assembly checkpoint is satisfied, cyclin B1 is very rapidly degraded. Cyclin B1 destruction continues throughout the following G1 phase but stops once cells begin DNA replication. These events have been visualised in real time by micro-injection of fluorescently labelled cyclin B1 into living cells (Clute and Pines, Nature Cell Biology, (1999), 1, 82–87).

The controlling elements which regulate temporal expression and destruction have been elucidated in a number of studies. Biosynthesis of cyclin B1 has been shown to be controlled at the level of transcription by a promoter sequence that confines expression to the late S and G2 phases of the cell cycle (Piaggio et al, Exp. Cell. Research, (1995), 216, 396–402; Cogswell et al, Mol. Cell. Biology, (1995), 15, 2782–2790). Destruction of cyclin B1 at the appropriate time in M phase has been shown to be controlled by a 9 amino acid sequence, termed the destruction box (D-box) which targets the protein for proteolysis via ubiquitinylation. Expression of a *Drosophila* cyclin B-GFP fusion protein driven by a constitutive polyubiquitin promoter (Huang and Raff, EMBO Journal, (1999), 18(8), 2184–2195) has shown that fluorescently-tagged cyclin B mimics the behaviour of endogenous cyclin B in being degraded at the end of metaphase. Studies (Hagting et al, Current Biology, (1999), 9, 680–689) using human cyclin B1-GFP have shown that temporal changes in cytoplasmic and nuclear localisation of cyclin B1 with cell cycle progression is dependent on a nuclear export signal (NES), phosphorylation of which leads to nuclear import.

Other cell cycle checkpoints are similarly regulated by temporal and spatial control mechanisms and many of the components and interrelationships have been elucidated (Pines, J., Nature Cell Biology, (1999), 1, E73–E79).

A number of methods have been described which make use of certain components of the cell cycle control mechanisms to provide procedures which analyse or exploit cell proliferation status.

WO 00/29602 describes use of a cyclin A promoter to drive expression of GFP as a selectable marker for dividing transgenic stem cells to allow dividing cells to be isolated from a background of non-dividing cells by fluorescence activated cell sorting. While this method allows identification and selection of cells which have progressed past a certain stage in the cell cycle, it does not yield information on the cell cycle status of any given cell, other than historical information that the cell has or has not passed through the G2 phase of the cell cycle at some time in the past.

U.S. Pat. No. 6,048,693 describes a method for screening for compounds affecting cell cycle regulatory proteins, wherein expression of a reporter gene is linked to control elements which are acted on by cyclins or other cell cycle control proteins. In this method, temporal expression of a reporter gene product is driven in a cell cycle specific fashion and compounds acting on one or more cell cycle control components may increase or decrease expression levels. Since the assay system contains no elements which provide for the destruction of the reporter gene product nor for destruction of any signal arising from the reporter gene, the method cannot yield information on the cell cycle position of any cells in the assay and reports only on general perturbations of cell cycle control mechanisms.

U.S. Pat. No. 5,849,508 and U.S. Pat. No. 6,103,887 describe methods for determining the proliferative status of cells by use of antibodies which bind to cyclin A. These methods provide means for determining the percentage of proliferating cells in a test population relative to a control population.

U.S. Pat. No. 6,159,691 relates to a method for assaying for putative regulators of cell cycle progression. In this method, nuclear localisation signals (NLS) derived from the cell cycle phase specific transcription factors DP-3 and E2F-1 are used to assay the activity of compounds which act as agonists or antagonists to increase or decrease nuclear localisation of an NLS fused to a detectable marker.

A number of researchers have studied the cell cycle using traditional reporter molecules that require the cells to be fixed or lysed. For example Hauser and Bauer (Plant and Soil, 2000, 226, p 1–10) used β-glucuronidase (GUS) to study cell division in a plant meristem and Brandeis and Hunt (EMBO J., 1996, vol 15, pp 5280–5289) used chloramphenical acetyl transferase (CAT) fusion proteins to study variations in cyclin levels. Although these methods provide a means of studying the cell cycle position of a particular cell (using GUS) or the average cell cycle status of a population of cells (using CAT) both methods are destructive. Neither method allows the repeated analysis of a specific cell over time and they are therefore not suitable to follow the progression of a cell through the cell cycle.

None of the preceding methods, which use components of the cell cycle control mechanism, provide means for determining the cell cycle status of an individual cell or a population of cells. Consequently, methods are required that enable the cell cycle position of a single living cell to be determined non-destructively, allowing the same cell to be repeatedly interrogated over time, and which enable the study of the effects of agents having potentially desired or undesired effects on the cell cycle. Furthermore, it is desirable for cell cycle position to be determined from a probe controlled directly by cell cycle control components, rather than indirectly through DNA content or other indirect markers of cell cycle position as described above. The present invention describes a method which utilises key components of the cell cycle regulatory machinery in defined combinations to provide novel means of determining cell cycle status for individual living mammalian cells in a non-destructive process providing dynamic read out.

The present invention provides DNA constructs, and cell lines containing such constructs, that exhibit activation and destruction of a detectable reporter molecule in a cell cycle phase specific manner, by direct linkage of reporter signal switching to temporal and spatial expression and destruction of cell cycle components. This greatly improves the precision of determination of cell cycle phase status and allows continuous monitoring of cell cycle progression in individual cells. Furthermore, it has been found that key control elements can be isolated and abstracted from functional elements of the cell cycle control mechanism to permit design of cell cycle phase reporters which are dynamically regulated and operate in concert with, but independently of, endogenous cell cycle control components, and hence provide means for monitoring cell cycle position without influencing or interfering with the natural progression of the cell cycle.

SUMMARY OF THE INVENTION

Accordingly, in a first aspect of the invention, there is provided a nucleic acid reporter construct comprising a nucleic acid sequence encoding a detectable live-cell reporter molecule operably linked to and under the control of:

i) at least one cell cycle phase-specific expression control element, and ii) a destruction control element;

wherein said reporter construct is expressed in a mammalian cell at a predetermined position in the cell cycle. Expression being defined as all of the processes involved in the biosynthesis of a protein from a gene. It will be further understood that the term 'live-cell', as it relates to reporter molecules, defines a reporter molecule which produces a detectable signal in living cells and is therefore suitable for use in live-cell imaging systems.

In a second aspect of the invention, there is provided a method for determining the position in the cell cycle of a mammalian cell said method comprising:

a) expressing in a cell a nucleic acid reporter construct comprising a nucleic acid sequence encoding a detectable live cell-reporter molecule operably linked to and under the control of:

i) at least one cell cycle phase-specific expression control element, and ii) a destruction control element;

wherein said reporter construct is expressed in a cell at a predetermined point in the cell cycle; and b) determining the position in the cell cycle by monitoring signals emitted by the reporter molecule.

In preferred embodiments of the first and second aspects, the nucleic acid reporter construct is also linked to and under the control of a cell cycle phase-specific spatial localisation control element.

Suitably, the nucleic acid reporter construct is a DNA construct.

The cell cycle phase-specific expression control element is typically a DNA sequence that controls transcription and/or translation of one or more nucleic acid sequences and permits the cell cycle specific control of expression. Any expression control element that is specifically active in one or more phases of the cell cycle may suitably be used for construction of the cycle position reporter construct.

Suitably, the cell cycle phase specific expression control element may be selected from cell cycle specific promoters and other elements that influence the control of transcription or translation in a cell cycle specific manner. Where the expression control element is a promoter, the choice of promoter will depend on the phase of the cell cycle selected for study.

Suitable promoters include: cyclin B1 promoter (Cogswell et al, Mol. Cell. Biol., (1995), 15(5), 2782–90, Hwang et al, J. Biol. Chem., (1995), 270(47), 28419–24, Piaggio et al, Exp. Cell Res., (1995), 216(2), 396–402); Cdc25B promoter (Korner et al, J. Biol. Chem., (2001), 276(13), 9662–9); cyclin A2 promoter (Henglein et al, Proc. Nat. Acad. Sci. USA, (1994), 91(12), 5490–4, Zwicker et al, Embo J., (1995), 14(18), 4514–22); Cdc2 promoter (Tommasi and Pfeifer, Mol. Cell Biol., (1995), 15(12), 6901–13, Zwicker et al, Embo J (1995), 14(18), 4514–22), Cdc25C promoter (Korner and Muller, J. Biol. Chem., (2000), 275 (25), 18676–81, Korner et al, Nucl. Acids Res., (1997), 25(24), 4933–9); cyclin E promoter (Botz et al, Mol. Cell Biol., (1996), 16(7), 3401–9, Korner and Muller, J. Biol. Chem., (2000), 275(25), 18676–81); Cdc6 promoter (Hateboer et al, Mol. Cell Biol., (1998), 18(11), 6679–97, Yan et al, Proc. Nat. Acad. Sci. USA, (1998), 95(7), 3603–8); DHFR promoter (Shimada et al, J. Biol. Chem., (1986), 261(3), 1445–52, Shimada and Nienhuis, J. Biol. Chem., (1985), 260(4), 2468–74) and histones promoters (van Wijnen et al, Proc. Nat. Acad. Sci. USA, (1994), 91, 12882–12886).

Suitably, the cell cycle phase specific expression control element may be selected from cell cycle specific IRES elements and other elements that influence the control of translation in a cell cycle specific manner. An IRES element is an internal ribosomal entry site that allows the binding of a ribosome and the initiation of translation to occur at a region of mRNA which is not the 5'-capped region. A cell cycle-specific IRES element restricts cap-independent initiation of translation to a specific stage of the cell cycle (Sachs, A. B., Cell, (2000), 101, 243–5). Where the expression control element is selected to be an IRES, suitably its selection will depend on the cell cycle phase under study. In this case, a constitutively expressed (eg. CMV or SV40) or inducible (eg. pTet-on pTet-off system, Clontech) promoter may be used to control the transcription of the bicistronic mRNA (Sachs, A. B., Cell, (2000), 101, 243–5). Alternatively, a non cell cycle phase-dependent IRES element (eg. the EMCV IRES found in pIRES vectors, BD Clontech) may be used in conjunction with a cell cycle specific promoter element. Alternatively, more precise control of expression of the reporter may be obtained by using a cell cycle phase specific promoter in conjunction with a cell cycle phase specific IRES element.

IRES elements suitable for use in the invention include: G2-IRES (Cornelis et al, Mol. Cell, (2000), 5(4), 597–605); HCV IRES (Honda et al, Gastroenterology, (2000), 118, 152–162); ODC IRES (Pyronet et al, Mol. Cell, (2000), 5, 607–616); c-myc IRES (Pyronnet et al, Mol. Cell, (2000), 5(4), 607–16) and p58 PITSLRE IRES (Cornelis et al, Mol. Cell, (2000), 5(4), 597–605).

Table 1 lists some preferred expression control elements that may be used in accordance with the invention, and indicates the cell cycle phase in which each element is activated.

TABLE 1

Cell Cycle Phase-Specific Expression Control Elements

| Element | Timing | Element | Timing |
|---|---|---|---|
| Cyclin B1 promoter | G2 | DHFR promoter | late G1 |
| Cdc25B promoter | S/G2 | Histones promoters | late G1/S |
| Cyclin A2 promoter | S | G2-IRES | G2 |
| Cdc2 promoter | S | HCV IRES | M |
| Cdc25C promoter | S | ODC IRES | G2/M |
| Cyclin E promoter | late G1 | c-myc IRES | M |
| Cdc6 promoter | late G1 | p58 PITSLRE IRES | G2/M |

The destruction control element is a DNA sequence encoding a protein motif that controls the destruction of proteins containing that sequence. Suitably, the destruction control element may be cell cycle mediated, for example: Cyclin B1 D-box (Glotzer et al, Nature, (1991), 349, 132–138, Yamano et al, EMBO J., (1998), 17(19), 5670–8, Clute and Pines, Nature Cell Biology, (1999), 1, 82–87); cyclin A N-terminus (den Elzen and Pines, J. Cell Biol., (2001), 153(1), 121–36, Geley et al, J. Cell Biol., (2001), 153, 137–48); KEN box (Pfleger and Kirschner, Genes Dev, (2000), 14(6), 655–65), Cyclin E (Yeh et al, Biochem Biophys Res Commun., (2001) 281, 884–90), Cln2 cyclin from *S. cerevisiae* (Berset et al, Mol. Cell Biol., (2002), pp 4463–4476) and p27Kip1 (Montagnoli et al, Genes Dev., (1999), 13(9), 1181–1189, Nakayama et al, EMBO J., (2000), 19(9), 2069–81, Tomoda et al, Nature, (1999), 398(6723), 160–5).

Table 2 lists destruction control elements that may be used according to the invention and indicates the cell cycle phase in which each element is activated.

Alternatively, the destruction control element may be non cell-cycle mediated, such as PEST sequences as described by Rogers et al, Science, (1986), 234, 364–8. Examples of non cell-cycle mediated destruction control elements include sequences derived from casein, ornithine decarboxylase and proteins that reduce protein half-life. Use of such non cell-cycle mediated destruction control sequences in the method of the invention provides means for determining the persistence time of the cell cycle reporter following induction of expression by a cell cycle specific promoter.

TABLE 2

Destruction Control Elements

| Element | Timing |
| --- | --- |
| Cyclin B1 D-box | Metaphase through to G1 phase |
| Cyclin A N-terminus | Prometaphase through to G1 phase |
| KEN box | anaphase/G1 |
| p27Kip1 | G1 |
| Cyclin E | G1/S boundary |
| Cln2 | G1/S boundary |

Suitably, the live-cell reporter molecule encoded by the nucleic acid sequence may be selected from the group consisting of fluorescent proteins and enzymes. Preferred fluorescent proteins include Green Fluorescent Protein (GFP) from *Aequorea Victoria* and derivatives of GFP such as functional GFP analogues in which the amino acid sequence of wild type GFP has been altered by amino acid deletion, addition, or substitution. Suitable GFP analogues for use in the present invention include EGFP (Cormack, B. P. et al, Gene, (1996), 173, 33–38); EYFP and ECFP (U.S. Pat. No. 6,066,476, Tsien, R. et al); F64L-GFP (U.S. Pat. No. 6,172,188, Thastrup, O. et al); BFP, (U.S. Pat. No. 6,077,707, Tsien, R. et al). Other fluorescent proteins include DsRed, HcRed and other novel fluorescent proteins (BD Clontech and Labas, Y. A. et al, Proc Natl Acad Sci USA (2002), 99, 4256–61) and *Renilla* GFP (Stratagene). Suitable enzyme reporters are those which are capable of generating a detectable (e.g. a fluorescent or a luminescent) signal in a substrate for that enzyme. Particularly suitable enzyme/substrates include: nitroreductase/Cy-Q (as disclosed in WO 01/57237) and β-lactamase/CCF4.

In a preferred embodiment according to the present invention, the nucleic acid reporter construct may optionally include a cell cycle phase-specific spatial localisation control element comprising a DNA sequence encoding a protein motif that is capable of controlling the sub-cellular localisation of the protein in a cell cycle specific manner. Such a localisation control element may be used advantageously according to the invention where:

i) a specific sub-cellular localisation of the reporter is desirable; and/or ii) more precise determination of the cell cycle position is required.

It may be required to determine the sub-cellular localisation of the reporter either to ensure its effective operation and/or destruction. More precise determination of the cell cycle position may be possible using a localisation control element since this will permit measurement of both intensity and location of the reporter signal.

Suitable spatial localisation control elements include those that regulate localisation of a cell cycle control protein, for example the cyclin B1 CRS.

Figure 2:
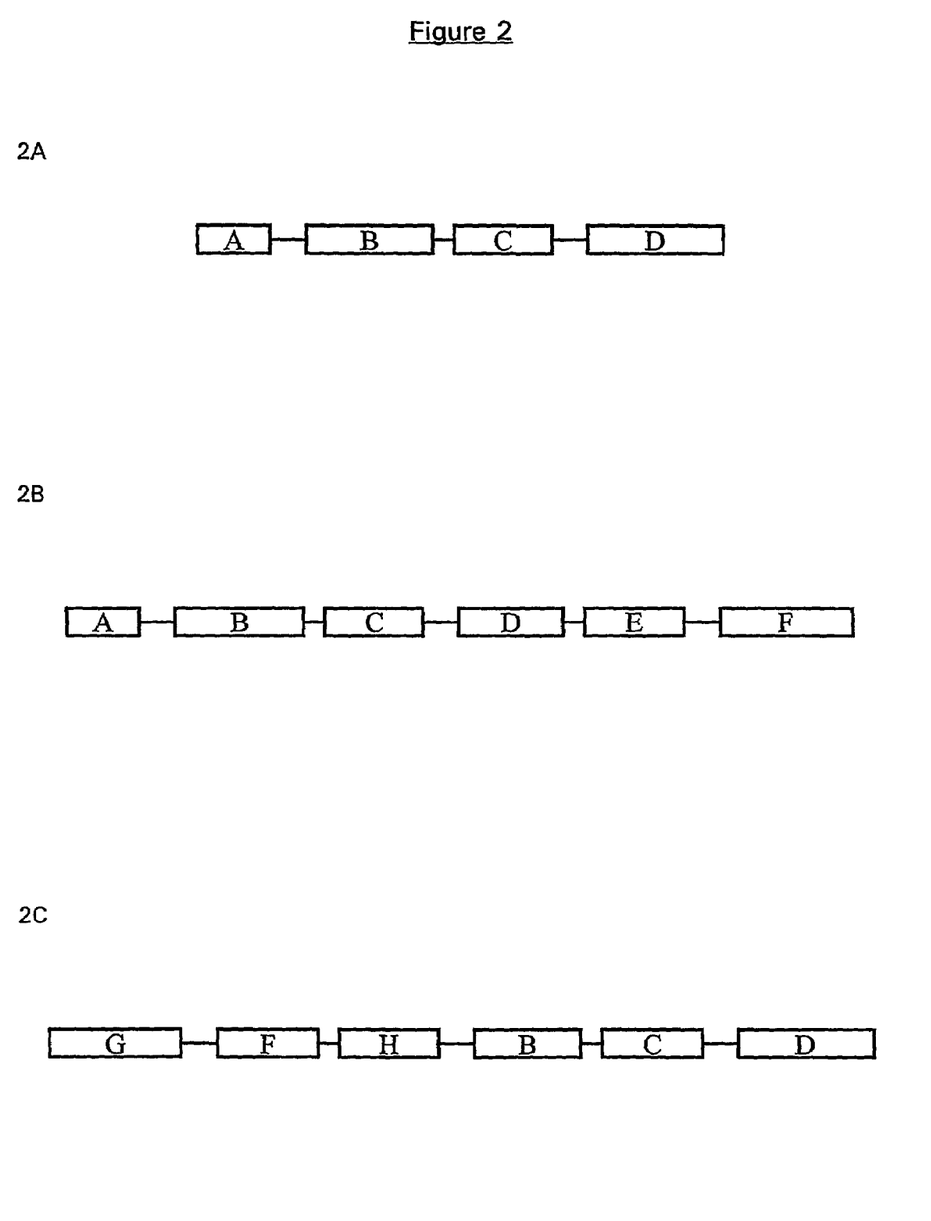
FIG. 2 is a schematic diagram illustrating cell cycle position nucleic acid reporter constructs according to the present invention and in which, 2A utilises a cell cycle phase-specific promoter and no IRES element, 2B utilises an IRES element to facilitate mammalian selection, and 2C contains a constituitive or inducible mammalian promoter and a cell cycle phase-specific IRES as the expression control element. In each case A represents a cell cycle phase-specific expression control (promoter), B represents a cell cycle phase specific destruction control element, C represents a cell cycle phase specific localisation control element, D represents a reporter gene, E represents a non-cell cycle specific IRES element, F represents a mammalian selectable marker, G represents a mammalian constitutive promoter and H represents a cell cycle specific IRES element.

The term, operably linked indicates that the elements are arranged so that they function in concert for their intended purposes, e.g. transcription initiates in a promoter and proceeds through the DNA sequence coding for the fluorescent protein of the invention. FIG. 2 (2A/2B/2C) illustrates the general construction of a DNA construct according to the invention.

In a preferred aspect of the invention, the construct comprises a cyclin B1 promoter, a cyclin B1 destruction box (D-box), a cyclin B1 cytoplasmic retention sequence (CRS) and a green fluorescent protein (GFP).

In a particular example according to the present invention, the nucleic acid reporter construct comprises an expression vector comprising the following elements:

a) a vector backbone comprising:
  i) a bacterial origin of replication; and
  ii) a bacterial drug resistance gene;

b) a cell cycle phase specific expression control element;

c) a destruction control element; and d) a nucleic acid sequence encoding a reporter molecule.

Optionally, the nucleic acid reporter construct additionally contains a cell cycle phase-specific spatial localisation control element and/or a eukaryotic drug resistance gene, preferably a mammalian drug resistance gene.

Expression vectors may also contain other nucleic acid sequences, such as polyadenylation signals, splice donor/splice acceptor signals, intervening sequences, transcriptional enhancer sequences, translational enhancer sequences and the like. Optionally, the drug resistance gene and the reporter gene may be operably linked by an internal ribosome entry site (IRES), which is either cell cycle specific (Sachs, et al, Cell, (2000), 101, 243–245) or cell cycle independent (Jang et al, J. Virology, (1988), 62, 2636–2643 and Pelletier and Sonenberg, Nature, (1988), 334, 320–325), rather than the two genes being driven from separate promoters. When using a non cell-cycle specific IRES element the pIRES-neo and pIRES-puro vectors commercially available from Clontech may be used.

Figure 3:
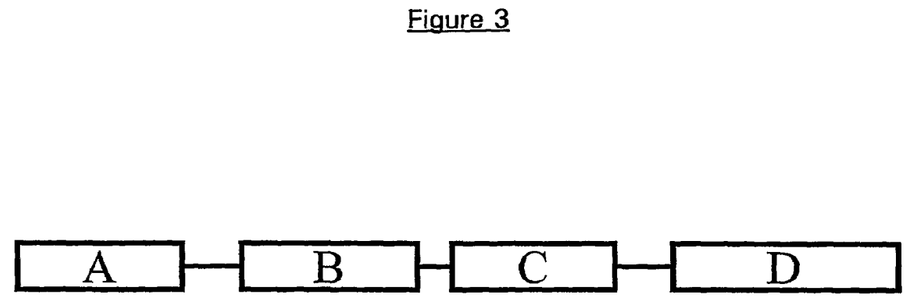
FIG. 3 shows a DNA construct for determining the G2/M phase of the cell cycle, the construct containing a cyclin B1 promoter (A), cyclin B1 destruction box (D-box) (B), cyclin B1 CRS(C) and a GFP reporter (D).
Figure 4:
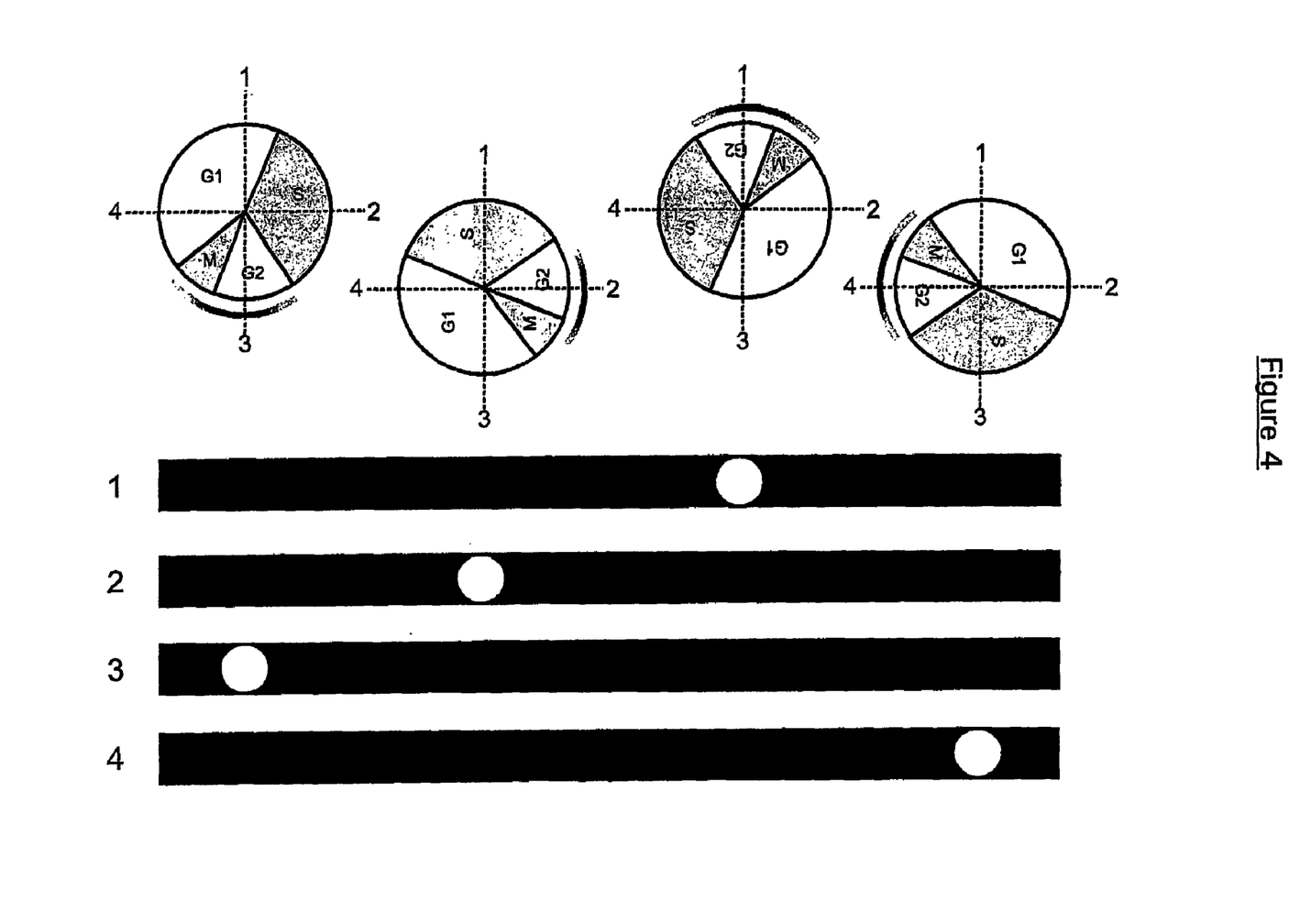
FIG. 4 illustrates the expression of a nucleic acid construct expressing the G2/M cell cycle phase marker in a population of unsynchronised cells. Each cell exhibits cyclical expression and destruction of the fluorescent product from the construct, resulting in a continuous "blinking" pattern of fluorescence from all cells in the population. Analysis of the fluorescence intensity of each cell at times 1, 2, 3 and 4 yields dynamic information on the cell position status of each cell.

In a particular embodiment of the first aspect, the nucleic acid reporter construct is assembled from a DNA sequence encoding the cyclin B1 promoter operably linked to DNA sequences encoding 171 amino acids of the amino terminus of cyclin B1 and a DNA sequence encoding a green fluorescent protein (GFP) (FIG. 3). Motifs controlling the localisation and destruction of cyclin B1 have all been mapped to ~150 amino acids in the amino terminus of the molecule. Consequently, an artificial cell cycle marker can be constructed using only sequences from the amino terminus of cyclin B1, which will not interfere with cell cycle progression since it lacks a specific sequence, termed the cyclin box, (Nugent et al, J. Cell. Sci., (1991), 99, 669–674) which is required to bind to and activate a partner kinase. Key regulatory motifs required from the amino terminus sequence of cyclin B1 are: i) a nine amino acid motif termed the destruction box (D-box). This is necessary to target cyclin B1 to the ubiquitination machinery and, in conjunction with at least one C-terminal lysine residue, this is also required for its cell-cycle specific degradation; ii) an approximately ten amino acid nuclear export signal (NES). This motif is recognised, either directly or indirectly, by exportin 1 and is sufficient to maintain the bulk of cyclin B1 in the cytoplasm throughout interphase; iii) approximately four mitosis-specific phosphorylation sites that are located in and adjacent to the NES and confer rapid nuclear import and a reduced nuclear export at mitosis. When expressed in a eukaryotic cell, the construct will exhibit cell cycle specific expression and destruction of the GFP reporter which parallels the expression and degradation of endogenous cyclin B1. Hence, measurement of GFP fluorescence intensity permits identification of cells in the G2/M phase of the cell cycle (FIG. 4). Furthermore, since the fluorescent product of the construct will mimic the spatial localisation of endogenous cyclin B1, analysis of the sub-cellular distribution of fluorescence permits further precision in assigning cell cycle position. At prophase, cyclin B1 rapidly translocates into the nucleus, consequently the precise localisation of GFP fluorescence in the cell can be used to discriminate cells transitioning from interphase to mitosis. Once a cell reaches metaphase, and the spindle assembly checkpoint is satisfied, cyclin B1 is very rapidly degraded, and consequently the disappearance of GFP fluorescence can be used to identify cells at mid-M phase.

Expression of the construct in a population of unsynchronised cells will result in each cell exhibiting cyclical expression and destruction of the fluorescent product from the construct, resulting in a continuous blinking pattern of fluorescence from all cells in the population. Analysis of the fluorescence intensity of each cell with time consequently yields dynamic information on the cell cycle status of each cell as illustrated in FIG. 4.

Further embodiments of the nucleic acid reporter construct according to the first aspect may be constructed by selecting suitable alternative cell cycle control elements, for example from those shown in Tables 1 and 2, to design cell cycle phase reporters which report a desired section of the cell cycle.

The construction and use of expression vectors and plasmids are well known to those of skill in the art. Virtually any mammalian cell expression vector may be used in connection with the cell cycle markers disclosed herein. Examples of suitable vector backbones which include bacterial and mammalian drug resistance genes and a bacterial origin of replication include, but are not limited to: pCI-neo (Promega), pcDNA (Invitrogen) and pTriEx1 (Novagen). Suitable bacterial drug resistance genes include genes encoding for proteins that confer resistance to antibiotics including, but not restricted to: ampicillin, kanamycin, tetracyclin and chloramphenicol. Eurkaryotic drug selection markers include agents such as: neomycin, hygromycin, puromycin, zeocin, mycophenolic acid, histidinol, gentamycin and methotrexate.

The DNA construct may be prepared by the standard recombinant molecular biology techniques of restriction digestion, ligation, transformation and plasmid purification by methods familiar to those skilled in the art and are as described in Sambrook, J. et al (1989), Molecular Cloning—A Laboratory Manual, Cold Spring Harbor Laboratory Press. Alternatively, the construct can be prepared synthetically by established methods, eg. the phosphoramidite method described by Beaucage and Caruthers, (Tetrahedron Letters, (1981), 22, 1859–1869) or the method described by Matthes et al (EMBO J., (1984), 3, 801–805). According to the phosphoramidite method, oligonucleotides are synthesised, eg. in an automatic DNA synthesizer, purified, annealed, ligated and cloned into suitable vectors. The DNA construct may also be prepared by polymerase chain reaction (PCR) using specific primers, for instance, as described in U.S. Pat. No. 4,683,202 or by Saiki et al (Science, (1988), 239, 487–491). A review of PCR methods may be found in PCR protocols, (1990), Academic Press, San Diego, Calif., U.S.A.

During the preparation of the DNA construct, the gene sequence encoding the reporter must be joined in frame with the cell cycle phase specific destruction control element and optionally the spatial localisation control element. The resultant DNA construct should then be placed under the control of one or more suitable cell cycle phase specific expression control elements.

In a third aspect, there is provided a host cell transfected with a nucleic acid reporter construct according to the present invention. The host cell into which the construct or the expression vector containing such a construct is introduced, may be any mammalian cell which is capable of expressing the construct.

The prepared DNA reporter construct may be transfected into a host cell using techniques well known to the skilled person. One approach is to temporarily permeabilise the cells using either chemical or physical procedures. These techniques may include: electroporation (Tur-Kaspa et al, Mol. Cell Biol. (1986), 6, 716–718; Potter et al, Proc. Nat. Acad. Sci. USA, (1984), 81, 7161–7165), a calcium phosphate based method (eg. Graham and Van der Eb, Virology, (1973), 52, 456–467 and Rippe et al, Mol. Cell Biol., (1990), 10, 689–695) or direct microinjection.

Alternatively, cationic lipid based methods (eg. the use of Superfect (Qiagen) or Fugene6 (Roche) may be used to introduce DNA into cells (Stewart et al, Human Gene Therapy, (1992), 3, 267; Torchilin et al, FASEB J, (1992), 6, 2716; Zhu et al, Science, (1993), 261, 209–211; Ledley et al, J. Pediatrics, (1987), 110, 1; Nicolau et al, Proc. Nat. Acad. Sci., USA, (1983), 80, 1068; Nicolau and Sene, Biochem. Biophys. Acta, (1982), 721, 185–190). Jiao et al, Biotechnology, (1993), 11, 497–502) describe the use of bombardment mediated gene transfer protocols for transferring and expressing genes in brain tissues which may also be used to transfer the DNA into host cells.

A further alternative method for transfecting the DNA construct into cells, utilises the natural ability of viruses to enter cells. Such methods include vectors and transfection protocols based on, for example, Herpes simplex virus (U.S. Pat. No. 5,288,641), cytomegalovirus (Miller, Curr. Top. Microbiol. Immunol., (1992), 158, 1), vaccinia virus (Baichwal and Sugden, 1986, in Gene Transfer, ed. R. Kucherlapati, New York, Plenum Press, p 117–148), and adenovirus and adeno-associated virus (Muzyczka, Curr. Top. Microbiol. Immunol., (1992), 158, 97–129).

Examples of suitable recombinant host cells include HeLa cells, Vero cells, Chinese Hamster ovary (CHO), U2OS, COS, BHK, HepG2, NIH 3T3 MDCK, RIN, HEK293 and other mammalian cell lines that are grown in vitro. Such cell lines are available from the American Tissue Culture Collection (ATCC), Bethesda, Md., U.S.A. Cells from primary cell lines that have been established after removing cells from a mammal followed by culturing the cells for a limited period of time are also intended to be included in the present invention.

Cell lines which exhibit stable expression of a cell cycle position reporter may also be used in establishing xenografts of engineered cells in host animals using standard methods. (Krasagakis, K. J et al, Cell Physiol., (2001), 187(3), 386–91; Paris, S. et al, Clin. Exp. Metastasis, (1999), 17(10), 817–22). Xenografts of tumour cell lines engineered to express cell cycle position reporters will enable establishment of model systems to study tumour cell division, stasis and metastasis and to screen new anticancer drugs.

Use of engineered cell lines or transgenic tissues expressing a cell cycle position reporter as allografts in a host animal will permit study of mechanisms affecting tolerance or rejection of tissue transplants (Pye D and Watt, D. J., J. Anat., (2001), 198 (Pt 2), 163–73; Brod, S. A. et al, Transplantation (2000), 69(10), 2162–6).

To perform the method for determining the cell cycle position of a cell according to the second aspect, cells transfected with the DNA reporter construct may be cultured under conditions and for a period of time sufficient to allow expression of the reporter molecule at a specific stage of the cell cycle. Typically, expression of the reporter molecule will occur between 16 and 72 hours post transfection, but may vary depending on the culture conditions. If the reporter molecule is based on a green fluorescent protein sequence the reporter may take a defined time to fold into a conformation that is fluorescent. This time is dependent upon the primary sequence of the green fluorescent protein derivative being used. The fluorescent reporter protein may also change colour with time (see for example, Terskikh, Science, (2000), 290, 1585–8) in which case imaging is required at specified time intervals following transfection.

The cell cycle position of the cells may be determined by monitoring the expression of the reporter molecule and detecting signals emitted by the reporter using an appropriate detection device. If the reporter molecule produces a fluorescent signal, then, either a conventional fluorescence microscope, or a confocal based fluorescence microscope may be used. If the reporter molecule produces luminescent light, then a suitable device such as a luminometer may be used. Using these techniques, the proportion of cells expressing the reporter molecule may be determined. If the DNA construct contains translocation control elements and the cells are examined using a microscope, the location of the reporter may also be determined. In the method according to the present invention, the fluorescence of cells transformed or transfected with the DNA construct may suitably be measured by optical means in for example; a spectrophotometer, a fluorimeter, a fluorescence microscope, a cooled charge-coupled device (CCD) imager (such as a scanning imager or an area imager), a fluorescence activated cell sorter, a confocal microscope or a scanning confocal device, where the spectral properties of the cells in culture may be determined as scans of light excitation and emission.

In the embodiment of the invention wherein the nucleic acid reporter construct comprises a drug resistance gene, following transfection and expression of the drug resistance gene (usually 1–2 days), cells expressing the modified reporter gene may be selected by growing the cells in the presence of an antibiotic for which transfected cells are resistant due, to the presence of a selectable marker gene. The purpose of adding the antibiotic is to select for cells that express the reporter gene and that have, in some cases, integrated the reporter gene, with its associated promoter, IRES elements, enhancer and termination sequences into the genome of the cell line. Following selection, a clonal cell line expressing the construct can be isolated using standard techniques. The clonal cell line may then be grown under standard conditions and will express reporter molecule and produce a detectable signal at a specific point in the cell cycle.

Cells transfected with the nucleic acid reporter construct according to the present invention may be grown in the absence and/or the presence of a test system to be studied and whose effect on the cell cycle of a cell is to be determined. By determining the proportion of cells expressing the reporter molecule and, optionally, the localisation of the signal within the cell, it is possible to determine the effect of the test system on the cell cycle of the cells, for example, whether the test system arrests the cells in a particular stage of the cell cycle, or whether the effect is to speed up or slow down cell division.

Thus, in a fourth aspect, there is provided a method of determining the effect of a test system on the cell cycle position of a mammalian cell, said method comprising:

a) expressing in a cell in the absence and in the presence of said test system a nucleic acid reporter construct comprising a nucleic acid sequence encoding a detectable live-cell reporter molecule operably linked to and under the control of:

i) at least one cell cycle phase-specific expression control element, and ii) a destruction control element;

wherein said reporter construct is expressed in a cell at a predetermined point in the cell cycle; and b) determining the cell cycle position by monitoring signals emitted by the reporter molecule wherein a difference between the emitted signals measured in the absence and in the presence of said test system is indicative of the effect of said test system on the cell cycle position of said cell.

In a fifth aspect, there is provided a method of determining the effect of a test system on the cell cycle position of a mammalian cell, the method comprising:

a) expressing in the cell in the presence of the test system a nucleic acid reporter construct comprising a nucleic acid sequence encoding a detectable live-cell reporter molecule operably linked to and under the control of:

i) at least one cell cycle phase-specific expression control element, and ii) a destruction control element;

wherein the reporter construct is expressed in a cell at a predetermined point in the cell cycle; and b) determining the cell cycle position by monitoring signals emitted by the reporter molecule, c) comparing the emitted signal in the presence of the test system with a known value for the emitted signal in the absence of the test system;

wherein a difference between the emitted signal measured in the presence of the test system and the known value in the absence of the test system is indicative of the effect of the test system on the cell cycle position of the cell.

In a sixth aspect, there is provided a method of determining the effect of a test system on the cell cycle position of a mammalian cell, said method comprising:

a) providing cells containing a nucleic acid reporter construct comprising a nucleic acid sequence encoding a detectable live-cell reporter molecule operably linked to and under the control of:

i) at least one cell cycle phase-specific expression control element, and ii) a destruction control element;

wherein the reporter construct is expressed in a cell at a predetermined point in the cell cycle;

b) culturing first and second populations of the cells respectively in the presence and absence of a test system and under conditions permitting expression of the nucleic acid reporter construct; and c) measuring the signals emitted by the reporter molecule in the first and second cell populations;

wherein a difference between the emitted signals measured in the first and second cell populations is indicative of the effect of the test system on the cell cycle position of the cell.

By the term test system, it is intended to mean an agent such as a drug, hormone, protein, peptide, nucleic acid and the like, to which the cell is exposed. Alternatively, the test system may be an agent such as a nucleic acid, peptide or protein that is expressed in the cell under study. For example, cells transfected with the nucleic acid reporter constructs according to the present invention may be used to determine whether expression of cDNA containing constructs encoding proteins under study have an effect on the cell cycle position of a cell. A series of cDNAs, inserted into a mammalian expression vector, may be transiently transfected into a cell stably expressing the cell cycle position reporter. By monitoring the expression and location of the nucleic acid reporter construct in these transfected cells, it is possible to determine the effects of the proteins encoded by the cDNAs on the cell cycle.

The cell cycle position nucleic acid reporter constructs according to the present invention may also be used in a method to determine the effect of the cell cycle position on a cellular process, or to determine the effect of the cell cycle position on the action of a test substance on a cellular process. It is well known that many cellular processes, including those that respond to external stimuli, are influenced by the cell cycle so as to operate or respond differently at different stages of the cell cycle. For example, endothelin receptors have been shown to be expressed at different levels during different phases of the cell cycle (Okazawa et al. J.

Biol. Chem., (1998), 273, 12584–12592) and consequently the sensitivity of cells to endothelin induced apoptosis varies with the cell cycle position. Similarly, cellular $Ca^{2+}$ mobilisation responses to vasopressin differ according to cell cycle position (Abel et al. J. Biol. Chem., (2000), 275, 32543–32551) due to variations in the route of signal transduction which utilise different G-proteins at different cell cycle phases. Use of the cell cycle position reporter constructs will allow cell to cell variations in a biological assay, measured using an appropriate assay reporter, to be correlated with the signal from a cell cycle position reporter in order to determine if any variations in the assay signal correlate with the cell cycle position reporter signal and hence determine any cell cycle dependence of the assay signal. For example, assays may be devised in which the amount of a red fluorescently labelled ligand bound to a cell surface receptor is correlated with cell cycle status determined using a GFP cell cycle position reporter. By cellular process, it is meant the normal processes which living cells undergo and includes: biosynthesis, uptake, transport, receptor binding, metabolism, fusion, biochemical response, growth and death.

Two or more cell cycle position nucleic acid reporter constructs may be used in combination in applications that include reporting on transition through two or more, cell cycle phases within the same cell. To achieve such duplex or multiplex reporting, two or more different constructs are engineered and expressed in the same cell, wherein each reporter construct comprises a different combination of control elements linked to a different and distinguishable reporter. For example, cellular expression of a construct comprising a cyclin B1 promoter and cyclin B1 D-box operably linked to GFP in combination with expression in the same cell of a second construct comprising a cyclin A2 promoter and cyclin B1 D-box operably linked to blue fluorescent protein (BFP) will allow discrimination of cells in S phase (blue fluorescence) from cells in G2/M phase (blue and green fluorescence).

The cell cycle position nucleic acid reporter constructs and assay methods according to the present invention may be used in a variety of additional applications, for example:

i) Cells transfected with the cell cycle position reporter constructs of the present invention may be used to determine the effect of the cell cycle on the expression, translocation or subcellular distribution of a second marker in a multiplexed assay. For example, if the intracellular translocation of a fluorescent reporter to the plasma membrane is being studied and it is found that a test compound results in translocation in a percentage of the cells, then, using cells transfected with a construct according to the invention, it is possible to determine whether the translocation was cell cycle dependent.

Thus, in a seventh aspect of the invention there is provided a method of determining the effect of the mammalian cell cycle on the expression, translocation or sub-cellular distribution of a first detectable reporter which is known to vary in response to a test system, the method comprising:
a) expressing in the cell in the presence of the test system a second nucleic acid reporter construct comprising a nucleic acid sequence encoding a detectable live-cell reporter molecule operably linked to and under the control of:

i) a cell cycle phase-specific expression control element, and ii) a destruction control element;

wherein the reporter construct is expressed in a cell at a predetermined point in the cell cycle;
b) determining the cell cycle position by monitoring signals emitted by the second reporter molecule;

c) monitoring the signals emitted by the first detectable reporter, wherein the relationship between cell cycle position determined by step b) and the signal emitted by the first detectable reporter is indicative of whether or not the expression, translocation or sub-cellular distribution of the first detectable reporter is cell cycle dependent. The term 'test system' is to be understood as hereinbefore described in relation to the fourth, fifth and sixth aspect of the present invention.

ii) Cell cycle position reporters of the present invention may be used in combination with analysis of endogenous cellular markers or phenomena that are cell cycle related, in order to gain further information on the cell cycle status of an individual cell or a cell population. For example, it is well known that the Golgi complex has a distinctive morphology in mammalian cells, comprising a ribbon like structure adjacent to the nucleus, and that distinctive changes occur in the structure of the Golgi as cells undergo mitosis as the ribbon structure is converted to clusters of vesicles and tubules dispersed throughout the mitotic cell. (Lowe et al., Trends Cell Biol., (1998), 8(1) 40–44). Analysis of the morphology of cell components, such as the Golgi apparatus, which vary in a known fashion with cell cycle progression, for example by use of specific fluorescent stains, may be used in combination with a cell cycle position reporter to enable more detailed analysis of cell cycle progression.

iii) The cell cycle position reporters according to the present invention may also be used for monitoring cell cycle status and progression in in-vivo applications. For example, the introduction of a DNA construct encoding a cell cycle reporter into living specimens such as *Xenopus* oocytes, and living organisms such as *C. elegans* and *Drosophila*, via transfection of individual cells or multiple cells can be achieved by microinjection (Krone P. H., and Heikkila J. J., Development, (1989), 106(2), 271–81), ballistic injection (Horard B. et al., Insect Mol. Biol., (1994), 3(4), 61–5), and other methods well known to the skilled person. Introduction of cell cycle reporter constructs into such specimens will enable investigation of cell cycle progression and control in cell progeny of transfected cells. Information from reporters is likely to be of significant value in study of growth and development in model organisms.

iv) The reporters of the present invention may be used in the generation of transgenic organisms, ie. where the DNA encoding the cell cycle position reporter is stably expressed in all cells of an organism or animal. Such transgenic organisms may be generated by microinjecting DNA into an early embryo, generally into one of the pronuclei of a newly fertilized egg. (Bishop J. O., Reprod. Nutr. Dev., (1996), 36(6), 607–18). Transgenic techniques may be used to engineer cell cycle position reporters into a range of host species from simple organisms such as *C. elegans* (Daniells, C. et al, Mutat. Res., (1998), 399(1), 55–64) to more complex organisms such as mice and rats (Sills, R. C., et al., Toxicol. Lett., (2001), 20(1–3), 187–98). Establishment of stable transgenic expression of a cell cycle position reporter in all cells of a transgenic organism will allow cell cycle status to be determined in any cell type within, or isolated from, the organism, including cultured cell lines derived from the organism. Accordingly, in an eighth aspect of the present invention there is provide a transgenic organism comprising a cell as hereinbefore described.

v) Cell lines that exhibit stable expression of a cell cycle position reporter may also be used in establishing xenografts of engineered cells in host animals using standard methods. (Krasagakis, K. J et al, Cell Physiol., (2001), 187(3), 386–91; Paris, S. et al, Clin. Exp. Metastasis, (1999), 17(10), 817–22). Thus, in a ninth aspect of the present invention, there is provided a cell line comprising a cell as hereinbefore described for use in establishing xenografts in a host organism. Xenografts of tumour cell lines engineered to express cell cycle position markers will enable establishment of model systems to study tumour cell division, stasis and metastasis and to screen new anticancer drugs.

vi) Use of engineered cell lines or transgenic tissues expressing a cell cycle position reporter as allografts in a host animal will permit study of mechanisms affecting tolerance or rejection of tissue transplants (Pye, D. and Watt, D. J., J. Anat., (2001), 198(Pt 2), 163–73; Brod, S. A. et al, Transplantation (2000), 69(10), 2162–6). Therefore, in a tenth aspect of the present invention there is provided a cell line comprising a cell as hereinbefore described for use in establishing allografts in a host organism.

In an eleventh aspect of the present invention there is provided a transgenic organism comprising a cell as hereinbefore described.

BRIEF DESCRIPTION OF THE DRAWINGS

The invention is further illustrated by reference to the following examples and figures in which.

DETAILED DESCRIPTION OF THE INVENTION

Examples

1. Preparation of DNA Construct i) The N-terminal third of the cyclin B1 mRNA (amino acids 1–171), encoding the cyclin B1 destruction box and the NES was amplified with HindIII and BamHI ends using standard PCR techniques and the following primers:

SEQ ID NO:1: GGGAAGCTTAGGATGGCGCTC-CGAGTCACCAGGAAC

SEQ ID NO:2: GCCGGATCCCACATATTCACTA-CAAAGGTT.

ii) The gene for wtGFP was amplified with primers designed to introduce restriction sites that would facilitate construction of fusion proteins. The PCR product was cloned into pTARGET (Promega) according to manufacturer's instructions and mutations (F64L/S175G/E222G) were introduced using the QuikChange site-directed mutagenesis kit (Stratagene). Constructs were verified by automated DNA sequencing. DNA encoding the mutant GFP was then cloned downstream of the cyclin B1 N-terminal region using BamHI and SalI restriction sites.

iii) The cell cycle dependent region of the cyclin B1 promoter (−150→+182) was amplified with SacII and HindIII sites and cloned upstream of the Cyclin B1 N-terminal region and the GFP fusion protein.

iv) The promoter and recombinant protein encoding DNA was excised and cloned in place of the CMV promoter in a BglII/NheI cut pCl-Neo derived vector.

2. Effect of Cell Cycle Blocking Agents on GFP Fluorescence from Cell Cycle Phase Marker Using Transiently Transfected Cells.

U20S cells (ATCC HTB-96) were cultured in wells of a 96 well microtitre plate. Cells were transfected with a cell cycle reporter construct prepared according to Example 1, comprising a cyclin B1 promoter operably linked to sequences encoding the cyclin B1 D-box, the cyclin B1 CRS, and GFP in a pCORON4004 vector (Amersham Biosciences) using Fugene 6 (Roche) as the transfection agent.

Following 24 hours of culture, cells were exposed to the specific cell cycle blockers mimosine (blocks at G1/S phase boundary) or demecolcine (blocks in M phase). Control cells were exposed to culture media alone.

Cells were incubated for a further 24 hours and then analysed for nuclear GFP expression using a confocal scanning imager with automated image analysis (IN Cell Analysis System, Amersham Biosciences).

Figure 5:
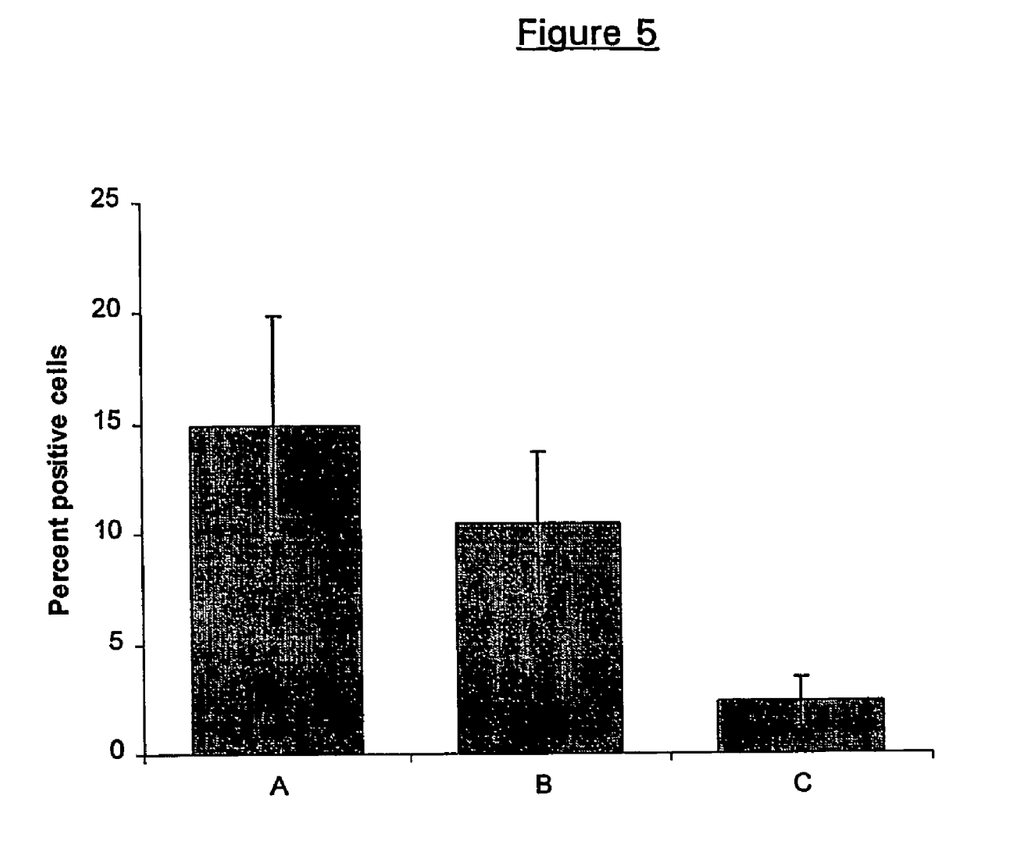
FIG. 5 is a bar chart showing the effect of cell cycle blocking agents on GFP fluorescence from a cell cycle phase marker according to the invention. A represents cells inhibited in mitosis by demecolchicine, B represents control cells and C represents cells inhibited at G1/S phase by mimosine.

As shown in FIG. 5, cells exposed to demecolcine showed increased fluorescence compared to control cells while cells exposed to mimosine showed decreased fluorescence compared to control cells. These results are consistent with the proposed use of the cell cycle phase reporter of the invention. Cells blocked in G1/S phase (mimosine treated), prior to the time of activation of the cyclin B1 promoter, show reduced fluorescence, while cells blocked in M phase (demecolcine treated), prior to the time of action of the cyclin B1 D-box, show increased fluorescence.

These results indicate that cell cycle phase reporters of the current invention are suitable for detecting agents which modulate cell cycle progression in a transient system and furthermore such reporters permit identification of the phase of the cell cycle in which cells are blocked.

3. Microinjection and Time-Lapse Photography of the Construct

Figure 6:
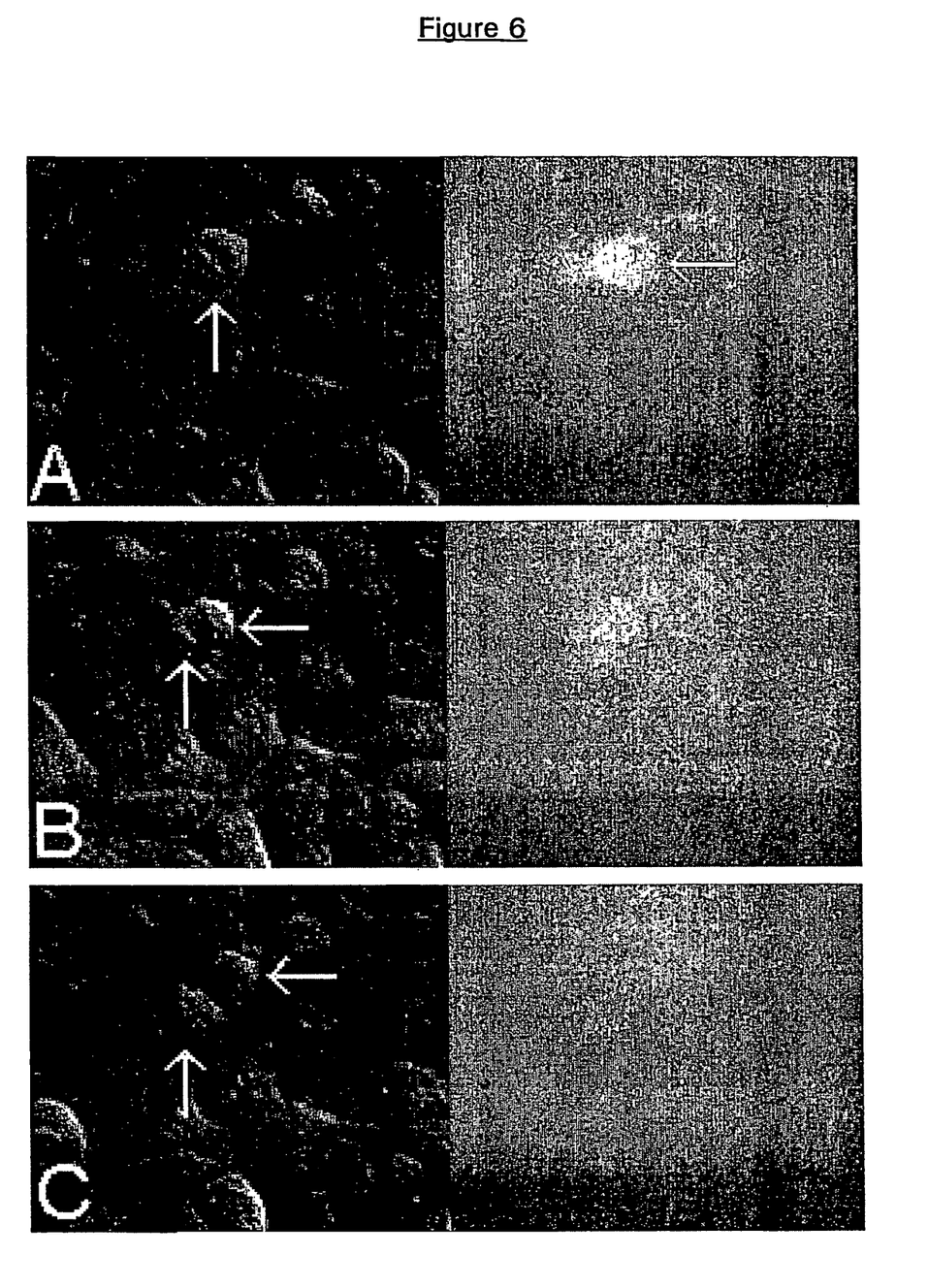
FIG. 6 is a series of time lapse photographs showing a cell that has been microinjected with the construct described in Example 1 and undergoing mitosis according to Example 3. Differential interference contrast (DIC) images are shown on the left with the corresponding fluorescence image on the right. Frame A shows a cell (arrowed) in metaphase which shows bright fluorescence in the nucleus. Frames B and C show the same cell at later times in anaphase (B) and late anaphase (C). The DIC images of B and C show the division of the cell into two daughter cells (indicated by 2 arrows), the corresponding fluorescence images show the loss of fluorescence accompanying destruction of the fluorescent construct as the cell cycle progresses.

HeLa cells were micro-injected with the construct prepared according to Example 1 and examined by time lapse microscopy, as shown in FIG. 6. Differential interference contrast (DIC) images are shown on the left with the corresponding fluorescence image on the right. Frame A shows a cell (arrowed) in metaphase which shows bright fluorescence in the nucleus. Frames B and C show the same cell at later times in anaphase (B) and late anaphase (C). The DIC images of B and C show the division of the cell into two daughter cells (indicated by 2 arrows), the corresponding fluorescence images show the loss of fluorescence accompanying destruction of the fluorescent construct as the cell cycle progresses.

4. Stable Cell Line Production and Time Lapse Photography

Figure 7:
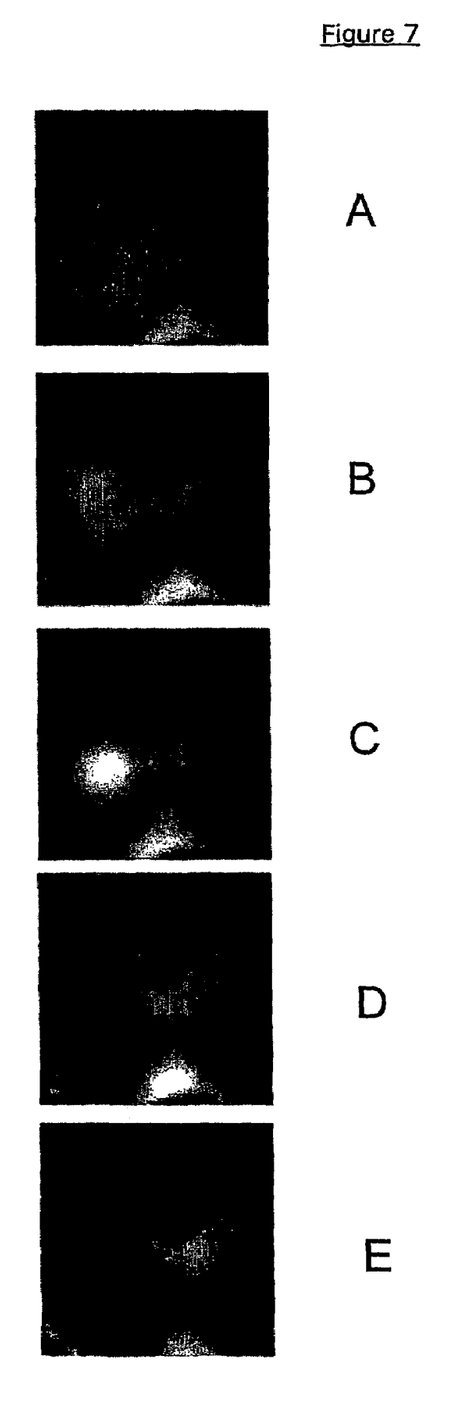
FIG. 7 is a series of time lapse photographs showing a U2-OS cell expressing the construct described in Example 1 undergoing mitosis according to Example 4. In panel A the cell on the left is in G2-phase of the cell cycle, in panel B the cell has entered prophase, in panel C the cell is in metaphase, in panel D the cell is in telophase and in panel E the two daughter cells are non-fluorescent and in G1 phase.

U2-OS cells (ATCC HTB-96) were transfected with the construct described in example 1 and grown for several months in culture media containing 1 mg/ml geneticin to select for cells stably expressing the construct. A number of clones were picked by standard methods (e.g. described in Freshney, Chapter 11 in Culture of Animal Cells, (1994) Wiley-Liss Inc) and a clone containing fluorescent cells was isolated. This cell line was maintained at 37° C. in culture media containing 25 mM HEPES and a fluorescence and transmitted image of the cells taken every 15 minutes over a period of 24 hours using a standard xenon lamp at 488 nm. FIG. 7 shows 5 frames from a portion of the image that indicates that the cell line is behaving as expected. Cells in G2 exhibit green fluorescence in the cytoplasm, cells in early mitosis have fluorescence predominantly in the nucleus and following mitosis the reporter gene is degraded and the cells lose their fluorescence.

Figure 8:
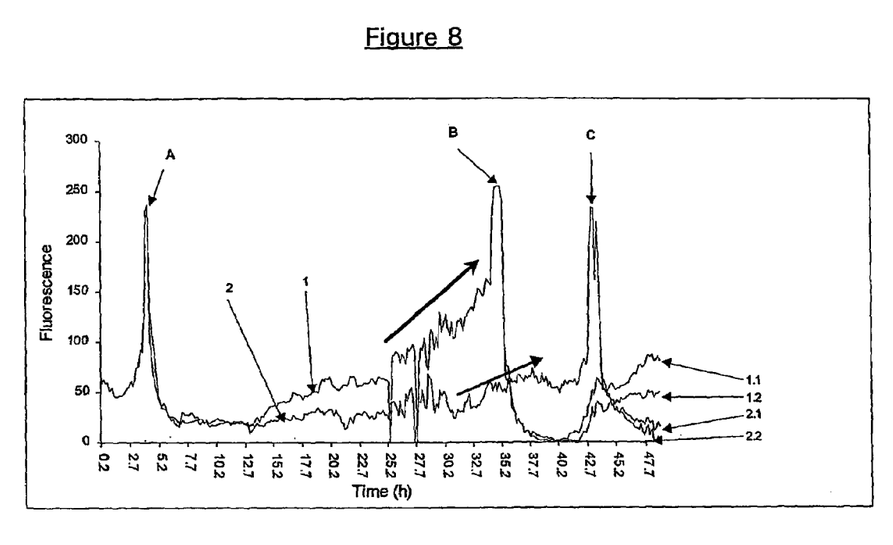
FIG. 8 is a graph showing the relative fluorescence of a U2-OS cell and its progeny that are stably expressing the construct described in Example 1 according to Example 4. The cell undergoes mitosis (A) after 4 hours and divides into two daughter cells (1,2). Daughter 1 then undergoes mitosis (B) at 34 hours dividing into two granddaughters (1.1 and 1.2) and Daughter 2 undergoes mitosis at 42 hours (C) dividing into granddaughters (2.1 and 2.2). The bold arrows show the increase in fluorescence of the daughter cells during G2-phase and prior to mitosis.

FIG. 8 shows the fate of a cell from the same clone that was monitored over 48 hours and that underwent two cell divisions to produce four granddaughter cells. For each time point the average intensity of each of the cells' progeny is measured and plotted against time. As can be seen the original cell enters mitosis at ~4 hours, one of the daughters divides at 32 hours and the other at 42 hours into the experiment. As cells leave S-phase and enter G2 there is a steady increase in average intensity until the cell enters mitosis when the cell rounds up and the average intensity increases dramatically.

5. Preparation of a Brighter Stable Cell Line and Subsequent FACS Analysis

The green fluorescent protein reporter sequence in the vector described in example 1 was replaced with enhanced GFP (EGFP; Cormack, B. P. et al, Gene, (1996), 173, 33–38; BD Clontech) by standard methods. The EGFP gene is a brighter form of GFP containing the mutations F64L and S65T. In addition, EGFP contains codons that have been altered to optimise expression in mammalian cells. This new construct was transfected into U2-OS cells and a number of colonies were isolated by selection with geneticin followed by sorting of single cells using a fluorescence activated cell sorter. These clones showed brighter fluorescence than those generated in example 4 and as expected fluorescence intensity and location appeared to vary according to the cell cycle phase of the cell.

The cells were prepared for FACS analysis by standard methods. Briefly the cells were fixed and permeabilised using CytoFix/CytoPerm (Becton Dickinson) according to the manufacturers procedures. The cells were then treated with 50 μg/ml RNAse and 0.4% Triton X-100 and counterstained with 100 μg/ml propidium iodide. The degree of propidium iodide staining is proportional to the amount of DNA in the cell and therefore a measure of the cell cycle phase of the cell. As expected, the degree of red propidium iodide staining and the amount of green GFP fluorescence appear to be proportional in the cells.

6. The Effect of Cell Cycle Inhibiting Drugs on GFP Expression Levels

Figure 9:
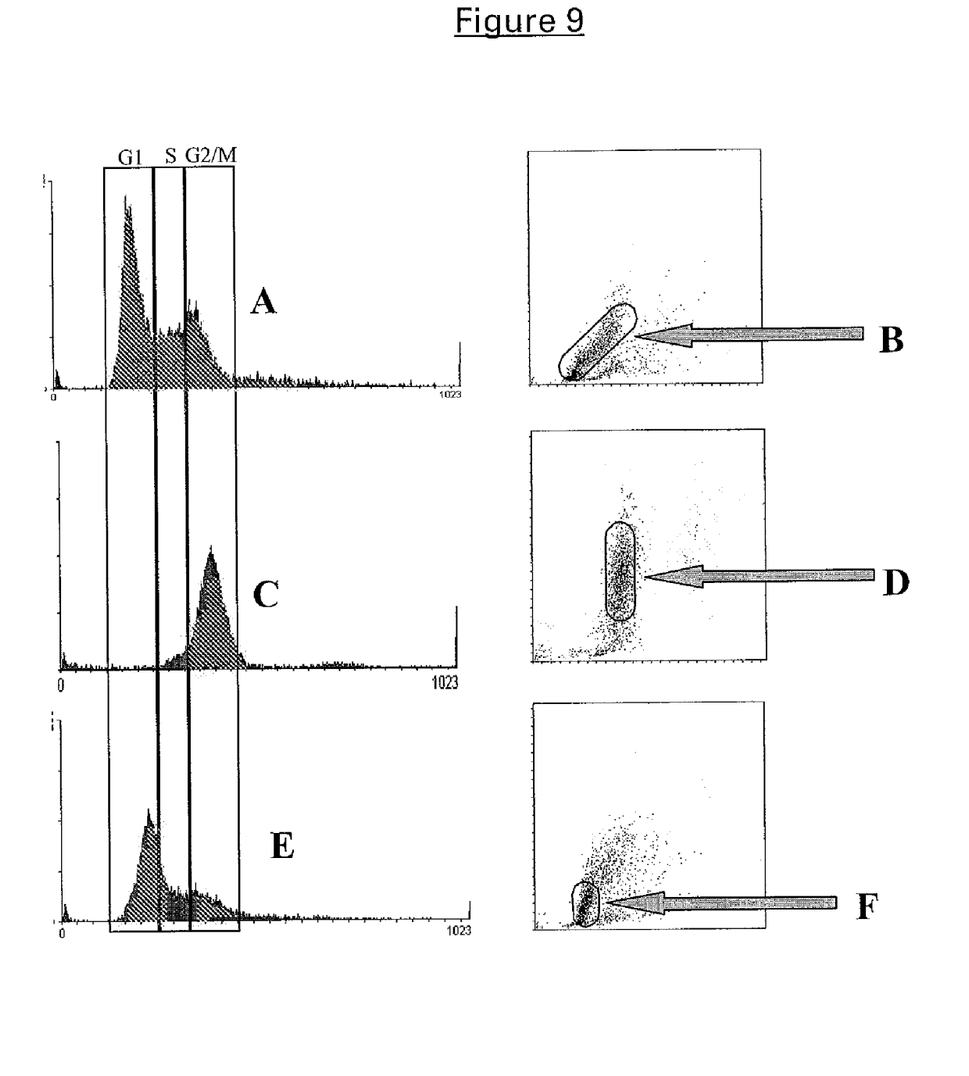
FIG. 9 is a FACS analysis showing the effect of cell cycle inhibitors upon the relative green fluorescence intensity of the stable cell line described in Example 5 according to Example 6. The histograms (on the left) show number of cells (Y-axis) against propidium iodide staining with FL3A (red fluorescence) and the dot-plots (on the right) show the same cells plotted with FL1H (green fluorescence, Y-axis) against FL3A (X-axis). The top two graphs show control cells that have not been treated with a cell cycle inhibitor. As can be seen these cells show the typical cell cycle profile (A) and have a diagonal pattern indicating that cells with more GFP are in the G2/M part of the cell cycle. The middle two graphs show cells that have been blocked in G2/M by colchicine (C). The majority of these cells have a relatively high green fluorescence (D). The bottom two graphs show cells that have been partially blocked in G1/S by mimosine (E). The majority of these cells have a relatively low green fluorescence (F).

The cells prepared in Example 5 were grown in 25 cm² flasks and treated with either 100 ng/ml demecolcine (Sigma) or 1 mM mimosine (Sigma) for 24 hours. The cells were then fixed, permeabilised and stained with propidium iodide as described in example 5. FACS analysis revealed that, as expected, cells treated with the colchicine analogue arrested in G2/M and cells treated with mimosine arrested at the G1/S boundary. As is also expected the cells that had been arrested in G2/M were brighter than the cells that had been arrested at G1/S (FIG. 9).

What is claimed is:

1. A nucleic acid reporter construct comprising a nucleic acid sequence encoding a fluorescent protein operably linked to and under the control of:
   i) a cyclin B1 promoter;
   ii) a cyclin B1 destruction box (D-box); and
   iii) a cyclin B1 cytoplasmic retention sequence (CRS).

2. The construct of claim 1, wherein said fluorescent protein is a Green Fluorescent Protein (GFP).

3. An isolated host cell transfected with the construct of claim 1, wherein said host cell is a mammalian host cell.

4. The isolated mammalian host cell of claim 3, wherein said host cell is selected from the group consisting of U2-OS cells and HeLa cells.

5. A nucleic acid reporter construct including an expression vector comprising:
   a) a vector backbone comprising:
      i) a bacterial origin of replication; and
      ii) a bacterial drug resistance gene;
   b) a cyclin B1 promoter;
   c) a cyclin B1 D-box;
   d) a nucleic acid sequence encoding a fluorescent protein; and
   e) a cyclin B1 CRS.

6. The construct of claim 5, further comprising a eukaryotic drug resistance gene.

* * * * *

SEQUENCE LISTING

<160> NUMBER OF SEQ ID NOS: 2

<210> SEQ ID NO 1
<211> LENGTH: 36
<212> TYPE: DNA
<213> ORGANISM: artificial sequence
<220> FEATURE:
<223> OTHER INFORMATION: synthetic oligonucleotide

<400> SEQUENCE: 1
gggaagctta ggatggcgct ccgagtcacc aggaac      36

<210> SEQ ID NO 2
<211> LENGTH: 30
<212> TYPE: DNA
<213> ORGANISM: artificial sequence
<220> FEATURE:
<223> OTHER INFORMATION: synthetic oligonucleotide

<400> SEQUENCE: 2
gccggatccc acatattcac tacaaaggtt      30